US009844521B2

(12) United States Patent
Kim et al.

(10) Patent No.: US 9,844,521 B2
(45) Date of Patent: Dec. 19, 2017

(54) PHARMACEUTICAL COMPOSITION COMPRISING GINGER EXTRACT OR SHOGAOL

(75) Inventors: Sun-Yeou Kim, Seoul (KR); Sang-Keun Ha, Busan (KR); Jong-Hoon Ryu, Seoul (KR); Myung-Sook Oh, Seongnam-si (KR); Seo-Young Jeong, Goyang-si (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 1650 days.

(21) Appl. No.: 13/130,009

(22) PCT Filed: Nov. 13, 2009

(86) PCT No.: PCT/KR2009/006664
§ 371 (c)(1),
(2), (4) Date: May 18, 2011

(87) PCT Pub. No.: WO2010/058926
PCT Pub. Date: May 27, 2010

(65) Prior Publication Data
US 2011/0229590 A1  Sep. 22, 2011

(30) Foreign Application Priority Data

Nov. 19, 2008  (KR) .................. 10-2008-0114964
Nov. 27, 2008  (KR) .................. 10-2008-0118582
Nov. 27, 2008  (KR) .................. 10-2008-0118585

(51) Int. Cl.
*A61K 31/12* (2006.01)
*A23L 33/105* (2016.01)

(52) U.S. Cl.
CPC ............ *A61K 31/12* (2013.01); *A23L 33/105* (2016.08); *A23V 2002/00* (2013.01)

(58) Field of Classification Search
CPC .. A61K 31/12; A23L 1/3002; A23V 2200/322
See application file for complete search history.

(56) References Cited

U.S. PATENT DOCUMENTS

| | | | |
|---|---|---|---|
| 6,518,315 B1 * | 2/2003 | Roufogalis | C07C 43/23 435/156 |
| 6,887,898 B1 | 5/2005 | Kim | |
| 7,049,455 B2 | 5/2006 | Kato et al. | |
| 7,279,501 B2 | 10/2007 | Kim | |
| 7,282,523 B2 | 10/2007 | Kim | |
| 7,455,860 B2 * | 11/2008 | Gokaraju | A23L 1/30 424/725 |
| 7,572,829 B2 | 8/2009 | Kim | |
| 7,728,043 B2 | 6/2010 | Kim | |
| 8,017,162 B2 * | 9/2011 | Shimoda | A61K 31/7008 424/756 |
| 8,226,989 B2 * | 7/2012 | Gokaraju | A61K 36/324 424/725 |
| 2005/0159611 A1 | 7/2005 | Kato et al. | |
| 2005/0197393 A1 | 9/2005 | Kim | |
| 2005/0239882 A1 | 10/2005 | Kim | |
| 2005/0260290 A1 * | 11/2005 | Raskin | A61K 31/192 424/756 |
| 2006/0040000 A1 * | 2/2006 | Gokaraju | A23L 1/30 424/725 |
| 2006/0148905 A1 | 7/2006 | Kim | |
| 2007/0154575 A1 * | 7/2007 | Shimoda | A61K 31/7008 424/756 |
| 2008/0085932 A1 | 4/2008 | Kim | |
| 2008/0193574 A1 | 8/2008 | Rishton et al. | |
| 2009/0285919 A1 * | 11/2009 | Alberte | A23L 1/3002 424/750 |

FOREIGN PATENT DOCUMENTS

| | | | |
|---|---|---|---|
| DE | 10320560 A1 * | 1/2004 | ........ A61K 36/9068 |
| JP | 361263909 A * | 11/1986 | |
| JP | 63-072625 A | 4/1988 | |
| JP | 02193930 A * | 7/1990 | |

OTHER PUBLICATIONS

Nakao et al. The effect of Shoseiryuto, a traditional Japanese medicine, on cytochrome P450s, N-acetyltransferase 2 and xanthine oxidase, in extensive or intermediatemetabolizers of CYP2D6; Eur J. Clin. Pharmacol (2007) 63: 345-353.*
Peirce, A. (Nov. 2004). Guide to natural healing: 2004 handbook for winter wellness. Psychology Today, 37, 73-75,77,79,81-82. Retrieved from http://search.proquest.com/docview/214485070?accountid=14753.*
Semwal et al. Gingerols and Shogaols: Important Nutraceutical Principles From Ginger; Phytochemistry, vol. 117, Sep. 2015, pp. 554-568.*
Yao, Y, B.S. (2007) Characterization of Cyclooxygenase-2 Inhibitors From Ginger Dietary Supplements; (Doctoral dissertation). Retrieved from ProQuest Dissertations and Theses, UMI No. 3294644, 162 pages.*
Third Party submission to USPTO from V.K. Gupta for U.S. Appl. No. 13/130,009 dated Nov. 1, 2011 with the following cited exhibits. 5 pages, including 1-2 of 20.
Bhārata Bhaisajya Ratnākara—Compiled by Nagīnadāsa Chaganalāla Śāha, Translated by Gopinath Gupta, vol.-V: B. Jain Publishers, New Delhi, Edn. 2nd. Reprint, Aug. 1999, p. 13. Formulation Id: HG/62, Formulation Name: Śunthīk vāthah. Publication (Prior art): p. 3 of 20. English Translation including Terminology Conversion (TKDL Extracts): p. 4-5 of 20.

(Continued)

Primary Examiner — Amy L Clark
(74) Attorney, Agent, or Firm — Nath, Goldberg & Meyer; Joshua B. Goldberg; Tanya E. Harkins

(57) ABSTRACT

The present invention provides a pharmaceutical composition for preventing or treating learning disorders, memory disorders, Parkinson's disease, or ischemic cerebrovascular disease, which comprises a ginger extract or shogaol; and a pharmaceutically acceptable carrier. And also, the present invention provides a food composition for improving learning disorders or memory disorders or alleviating the symptoms of learning disorders or memory disorders which comprises a ginger extract or shogaol as an active ingredient, or a food composition for improving learning or memory which comprises a ginger extract or shogaol as an active ingredient.

4 Claims, 12 Drawing Sheets

(56) References Cited

OTHER PUBLICATIONS

Āryabhisaka (Hindustāna Cā Vaidyarāja) by Śmkaradājīśāstrīpade. Published by Ramesh Vitthal Raghuvansī, Śri Gajānana book dipot, Bhavāniśankara road, Dādara, Mumbai on Aug. 15, 1973, p. 309. Formulation Id: RS 17/3532. Formulation Name: Sunthipaka-I. Publication (Prior art): p. 06. English Translation including Terminology Conversion (TKDL Extracts): p. 7-8 of 20.

Manthāna Bhairava; Ānandakandah. Edited with Tamil translation by S.V. Radhakrishna Sastri, T.M.S.S.M. Library, Tanjore, Madras, Edn. 1st, 1952, p. 221-222. Formulation Id: RS13/303. Formulation Name: Sunthi Kalpah. Publication (Prior art): p. 9 of 20. English Translation including Terminology Conversion (TKDL Extracts): p. 10 of 20.

Mohammad Akmal Khan; Qaraabaadeen Azam wa Akmal (20th century AD), Matba Siddiqi, Delhi / Matba, Mustafai, Delhi, 1909, p. 124. Formulation Id: BA3/764C. Formulation Name: Murabba Bara-e- Istirkha. Publication (Prior art): p. 11 of 20. English Translation including Terminology Conversion (TKDL Extracts): p. 12 of 20.

Aminuddaulah Abul Farj Ibn Al-Quff Maseehi; Kitaab-al-'Umdah-fil-Jeraahat, Part I (13th century AD), Dayerah-al-Ma'aarif Usmania, Hyderabad, 1937, p. 237. Formulation Id: MA 1/ 107. Formulation Name: Zanjabeel. Publication (Prior art): p. 13 of 20. English Translation including Terminology Conversion (TKDL Extracts): p. 14 of 20.

Abu Ali Ibn-e-Sina; Al~Qaanoon-fil-Tibb, vol. II (llth century AD), Institute of History of Medicine and Medical Research, Jamia Hamdard, New Delhi-62, 1987, p. 209. Formulation Id: AH1/ 331. Formulation Name: Zanjabeel. Publication (Prior art): p. 15 of 20. English Translation including Terminology Conversion (TKDL Extracts): p. 16 of 20.

Mohammad Akmal Khan; Qaraabaadeen Azam wa Akmal (20th century AD), Matba Siddiqi, Delhi / Matba. Mustafai, Delhi, 1909, p. 94. Formulation Id: BA3/614A. Formulation Name: Hareera Bara-e- Suda Zofi. Publication (Prior art): p. 17 of 20. English Translation including Terminology Conversion (TKDL Extracts): p. 18 of 20.

Mohammad Najmul Ghani Khan; Qaraabaadeen Najm-al-Ghani (20th century AD), Munshi Nawal Kishore, Lucknow, (Second Edition) 1928, p. 116. Formulation Id: NA4/651. Formulation Name: Jawarish Shoneez. Publication (Prior art): p. 19 of 20. English Translation including Terminology Conversion (TKDL Extracts): p. 20 of 20.

* cited by examiner

Control        Shogaol 20 μM

T-Ia

Sham

2VO

2VO + Ginger Ex. (25mg/kg)

PHARMACEUTICAL COMPOSITION COMPRISING GINGER EXTRACT OR SHOGAOL

This is a National Phase Application filed under 35 U.S.C. 371 as a national stage of PCT/KR2009/006664, filed on Nov. 13, 2009, and claims benefit from Korean Patent Application No. 10-2008-0114964, filed Nov. 19, 2008, and claims benefit form Korean Patent Application No. 10-2008-0118582, filed Nov. 27, 2008, and claims benefit from Korean Patent Application No. 10-2008-0118585, filed Nov. 27, 2008.

TECHNICAL FIELD

The present invention relates to a pharmaceutical composition for preventing or treating learning disorders, memory disorders, Parkinson's disease, or ischemic cerebrovascular disease, which comprises a ginger extract or shogaol; and a pharmaceutically acceptable carrier. And also, the present invention relates to a food composition for improving learning disorders or memory disorders or alleviating the symptoms of learning disorders or memory disorders which comprises a ginger extract or shogaol as an active ingredient, or a food composition for improving learning or memory which comprises a ginger extract or shogaol as an active ingredient.

BACKGROUND ART

Memory refers to a process in which new information from a surrounding environment, learned experiences, or knowledge are acquired, encoded and stored in a particular portion of the brain, and recalled (William F Ganong; Ganong's Physiology, Seoul, Hanwoori, p 289, p 291-292, 1999). The process of memory is classified as acquiring, encoding, enhancing, maintaining, and recalling. Modern society is moving toward a complicated and specialized society and correspondingly, a great amount of information and learning is required, and thus effective brain activities are required. Also, many people suffer from memory loss due to aging and disease, and as human lifetimes extend, humans require high-level mental activities. In order to appropriately cope with such cases, many efforts are being made, for example, mental activities are performed to clear the brain and improve memory, and development of pharmaceutical products and functional foods for effectively improving such functions are required in the art.

Parkinson's disease is a chronic progressive neurological disease and a representative intractable disease. Parkinson's disease develops due to sudden retrogression of cells that generate dopamine as a neurotransmitter or a significant decrease in the number of the cells in a substantia nigra portion of the mesencephalon. Although the cause of Parkinson's disease has not been clearly disclosed, it is known that the development of Parkinson's disease is related to cerebral arteriosclerosis, carbon-monoxide poisoning, medication, metabolic or traumatic encephalitis sequelae induced by hypoparathyroidism, etc. Due to the decrease of dopamine as a neurotransmitter, the balance of a neurotransmitter system is broken and thus tremor, rigidity, bradykinesia, and postural instability, which are representative symptoms of Parkinson's disease, develop.

As a therapeutic agent for Parkinson's disease, an L-dopa formulation, a dopamine receptor agonist, an anti-cholinergic agent, Eldepryl (or depreyl) etc. are known, and most of these drugs are used to control symptoms, instead of as a causal treatment, and accordingly, continuous drug administration is required. However, the long-term administration of drugs causes drug side effects. For example, anti-cholinergic agents may cause automatic nervous system disorders or mental function disorders, and thus, continuous administration thereof to old patients has a limitation. Also, regarding a Levodopa formulation, the long-term administration thereof leads to a gradual effect decrease and abnormal behavior such as body twisting or automatic movement of the hands or feet. In addition, neurostimulation using high frequency, that is, a surgical treatment such as high-frequency neurolysis or deep brain stimulation, may also be used, but these methods require invasive surgery and incur high costs.

Ischemic cerebrovascular disease or ischemia refers to a disease that causes a topical normal cerebral blood flow disorder due to various pathological abnormalities in blood vessels for supplying blood flow to the brain. Examples of ischemic cerebrovascular disease are transient ischemic attack (TIA), reversible ischemic neurologic deficit (RIND), progressing stroke, completed stroke, and ischemic vascular dementia. TIA refers to a case in which a topical neurological disorder occurs due to cerebral ischemia and recovery is within 24 hours, mostly within 10 to 15 minutes. RIND refers to a case in which although a topical ischemic symptom continues for 24 hours or more, the symptom is recovered within 3 weeks. Due to definite abnormal findings during neurological examination, RIND is clearly differentiated from TIA. Progressing stroke refers to a case in which a topical cerebral ischemia symptom is exacerbated for a few minutes to a few hours, and a cause thereof is extension of cerebral ischemia in a brain tissue of an already connected portion. The exacerbation of the topical cerebral ischemia symptom is different from exacerbation of neurological symptoms due to ischemic brain edema. Among patients having cerebral infarction in an internal carotid artery territory, about 20% experience a progressing stroke within first 48 hours, and in the case of a vertebrobasilar territory, about 40% experience a progressing stroke. Completed stroke refers to a case in which no neurological change occurs for a few days to a few months after the topical cerebral ischemia symptom occurs. Ischemic vascular dementia is a kind of vascular dementia, has a premise of two or more events of ischemic cerebral infarction, and does not necessarily require temporal causality with dementia.

Ginger (*Zingiber officinale Roscoe*) is a *Zingiber* genus plant that belongs to a Zingiberaceae plant, is widely distributed in the Southeast Asia, and has been used as folk medicine. As a ginger component, starch accounts for 40 to 60% in ginger, and ginger further consists of an aromatic hot flavor component, a resin protein, fiber, pentosan, an inorganic material, etc. As a hot flavor component of ginger, gingeron, gingerol, shogaol, and dihydrogingerol are known, and as an aromatic component of ginger, about 40 kinds of aromatic components of ginger, such as citral or camphene, are known. As ginger activities, an anti-oxidant activity (Masuda et al., Chem. Lett., 1, pp 189-192, 1993; Jitoe et al., Tetrahedron Lett., 35, pp 981-984, 1994), an anti-inflammation activity (Ozaki et al., Chem. Pharm. Bull., 39, pp 2353-2356, 1991; Jeenapongsa et al., J. Ethnopharmacol., 87, pp 143-148, 2003), a disinfestation activity (Nugroho et al., Phytochemistry, 41, pp 129-132, 1996), and a uterus relaxation activity (Kanjanaphthi et al., Planta Med., 53, pp 329-332, 1987) have been reported.

DETAILED DESCRIPTION OF THE INVENTION

Technical Problem

The present inventors screened various pharmacological activities of natural products (i.e., herbal extract) or compounds originated therefrom, which have high safety. As a result, surprisingly, it was found that a ginger extract and shogaol contained in ginger have an activity for improving learning ability and/or memory, and also an activity for preventing and/or treating Parkinson's disease and ischemic cerebrovascular disease.

Accordingly, the present invention provides a pharmaceutical composition for preventing or treating learning disorders, memory disorders, Parkinson's disease, or ischemic cerebrovascular disease, which comprises a ginger extract or shogaol; and a pharmaceutically acceptable carrier.

And also, the present invention provides a food composition for improving learning disorders or memory disorders or alleviating the symptoms of learning disorders or memory disorders which comprises a ginger extract or shogaol as an active ingredient, or a food composition for improving learning or memory which comprises a ginger extract or shogaol as an active ingredient.

Technical Solution

In accordance with an aspect of the present invention, there is provided a pharmaceutical composition for preventing or treating learning disorders, memory disorders, Parkinson's disease, or ischemic cerebrovascular disease, which comprises a ginger extract or shogaol as an active ingredient and a pharmaceutically acceptable carrier.

In accordance with another aspect of the present invention, there is provided a food composition for improving learning disorders or memory disorders or alleviating symptoms of learning disorder or memory disorders, which comprises a ginger extract or shogaol as an active ingredient.

In accordance with still another aspect of the present invention, there is provided a food composition for improving learning or memory, which comprises a ginger extract or shogaol as an active ingredient.

Advantageous Effects

It has been newly found by the present invention that a ginger extract or shogaol has an activity for preventing and/or treating learning disorders, memory disorders, Parkinson's disease, or ischemic cerebrovascular disease. Accordingly, a pharmaceutical composition according to the present invention may be effectively used in preventing or treating learning disorders, memory disorders, Parkinson's disease, or ischemic cerebrovascular disease. And also, a food composition including a ginger extract or shogaol as an active ingredient may be effectively used in improving learning disorders or memory disorders or alleviating the symptoms of learning disorders or memory disorders, and/or improving learning or memory.

BEST MODE

Figure 1:
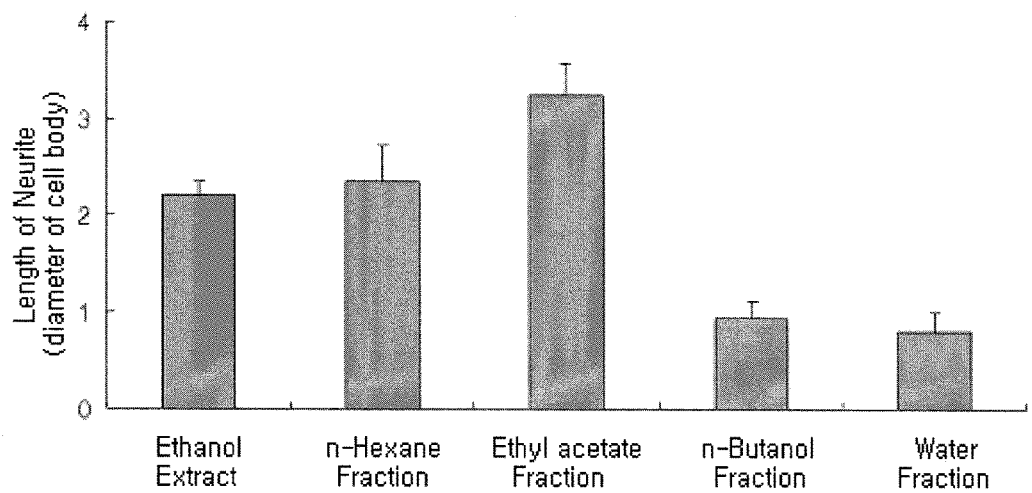
FIG. 1 shows neurite outgrowth effects of a ginger extract, which were obtained by evaluating length of neurite after the conditioned media prepared by treating an ethanol extract, an n-hexane fraction, an ethyl acetate fraction, a butanol fraction, and a water fraction of ginger in C6 cells were treated in PC12 cells.

The term "learning" used herein refers to an ability or behavior that perceives and changes one's behavior and may include a spatial perception ability, a cognitive ability, a concentration ability, etc.

The term "learning disorder or learning disability" used herein refers to a state in which a "learning" ability is lowered compared to that of a normal person due to various causes, for example, depression, anxiety, obsession, and socio-environmental factors (family trouble, poverty, a broken family, or stress), regardless an intelligence quotient, and the term "learning disorder or learning disability" includes a decrease in spatial perception, cognitive ability, concentration ability, and academic achievement of, for example, children, etc.

The term "memory" used herein refers to an ability of acquiring new information from a surrounding environment, learned experiences, or knowledge, encoding and storing them in a particular portion of the brain, and recalling them.

The term "memory disorder or memory deficiency" used herein refers to a state in which the "memory" has decreased compared to that of a normal person due to various reasons, such as trauma, attention deficit, aging, or disease, and the "memory disorder or memory deficiency" may include amnesia, concentration disorder, spatial perception loss, decrease in learning ability, perception loss, etc.

The term "ischemic cerebrovascular disease or Ischemia" used herein refers to a disease that causes a topical normal cerebral blood flow disorder due to various pathological abnormalities in blood vessels for supplying blood flow to the brain. Examples of ischemic cerebrovascular disease are transient ischemic attack (TIA), reversible ischemic neurologic deficit (RIND), progressing stroke, completed stroke, and ischemic vascular dementia. In particular, the "ischemic cerebrovascular disease" used herein includes a progressing and/or completed stroke.

It has been newly found by the present invention that a ginger extract or shogaol prevents or treats learning disorders or memory disorders and improves learning or memory. A ginger extract or shogaol was administered for 3 days and a passive avoidance task was performed. As a result, it was confirmed that when a ginger extract or shogaol was administered, learning and/or memory were substantially improved.

And also, it has been newly found by the present invention that a ginger extract or shogaol prevents or treats Parkinson's disease. Dopamine neurotoxicity was induced using 1-methyl-4-phenylpyridinium (MPP+) and 6-hydroxydopammine (6-OHDA) and then a test for evaluating a dopamine neuron protection activity was performed. As a result, it was confirmed that shogaol had a dopamine cell protection activity. Also, Parkinson's disease was induced in a mouse by using N-methyl-4-phenyl-1,2,3,6-tetrahydropyridine (MPTP), and a pole test and a dopaminergic neuron protection activity test were performed. When a ginger extract or shogaol was administered, MPTP-induced bradykinesia was restored, and also, excellent dopaminergic neuron protection activities were confirmed in striatum and substantia nigra.

In addition, it has been newly found by the present invention that a ginger extract or shogaol prevents or treats ischemic cerebrovascular disease. In a 2-vessel occlusion cerebral ischemia model, a ginger extract and shogaol showed excellent neuron apotosis suppression activities.

The present invention provides pharmaceutical composition for preventing or treating learning disorders, memory disorders, Parkinson's disease, or ischemic cerebrovascular disease, which comprises a ginger extract or shogaol as an active ingredient and a pharmaceutically acceptable carrier.

The ginger extract may be prepared by performing an extraction process comprising extracting a ginger with an extraction solvent selected from the group consisting of a $C_1$ to $C_4$ alcohol, n-hexane, ethyl acetate, n-butanol, chloroform, and a mixture thereof. Preferably, the ginger extract may be an ethanol-extract obtained by extracting a ginger with ethanol. An amount of the extraction solvent used is not limited. For example, the extraction solvent may be used in about 1 to 10 times of volume, preferably about 1 to 5 times of volume, to a weight of a ginger powder sample. And, the extraction may be performed by cold extraction, hot extraction, ultrasonic extraction, or refluxing cooling extraction for about 7 days to 20 days, preferably about 7 days to 10 days. Preferably, the extraction may be performed by cold extraction at room temperature (about 25° C.), and also, the extraction may be performed once or multiple times, for example, about 3 times. The obtained extraction solution may be treated by using a conventional method, for example, concentrated or dried under reduced pressure at a temperature of about 20 to 100° C., preferably about 30 to 70° C., thereby producing the ginger extract in a liquid or powder form.

The ginger extract may be subjected to an additional extraction process so as to increase an amount of active ingredients. That is, a ginger extract containing a high amount of active ingredients may be obtained by performing an extraction process comprising (a) extracting a ginger with a $C_1$ to $C_4$ alcohol; and (b) extracting the extract obtained from the step (a) with water and n-hexane, and then separating the resulting n-hexane layer. The extraction process may also include an additional chromatography fractionation step.

And also, a ginger extract containing a high amount of active ingredients may be obtained by performing an extraction process comprising (a) extracting a ginger using a $C_1$ to $C_4$ alcohol; (b') extracting the extract obtained from the step (a) with water and n-hexane, and then separating the resulting water layer; and (c) extracting the water layer obtained from step (b') with ethyl acetate, and then separating the resulting ethyl acetate layer. The extraction process may also include an additional chromatography fractionation step.

In addition, a ginger extract containing a high amount of active ingredients may be obtained by performing an extraction process comprising (a) extracting a ginger using a $C_1$ to $C_4$ alcohol; (b') extracting the extract obtained from the step (a) with water and n-hexane, and then separating the resulting water layer; (c') extracting the water layer obtained from step (b') with ethyl acetate, and then separating the resulting water layer; and (d) extracting the water layer obtained from step (c') with n-butanol, and then separating the resulting n-butanol layer or water layer. The extraction process may also include an additional chromatography fractionation step.

Preferably, the extraction process providing an ethyl acetate fraction may be used.

The additional extraction processes [that is, steps (b), (b'), (c), (c'), and (d)] may be performed by cold extraction at room temperature (about 25° C.), and also, the extraction processes may be performed once or multiple times, for example, about 3 times. The obtained extraction solution may be treated using a conventional method, for example, may be concentrated under reduced pressure or lyophilized according to a need at a temperature of about 20 to 100° C., for example, about 30 to 70° C., thereby producing the ginger extract in a liquid or powder form.

And also, after the additional extraction process is performed, if needed, a fractionation step may be performed using silica gel column chromatography. The fractionation step may be performed by repeatedly performing elution processes with elution solvents, while increasing polarities of a mixed solvent of hexane and ethyl acetate (Hexane:EtOAc=30:1→→1:11) and a mixed solvent of ethyl acetate and methanol (EtOAc:MeOH=25:1→→1:2).

The ginger extract may also be obtained by supercritical extraction. The supercritical extraction may be performed under a pressure of 60 to 350 bar, preferably about 300 bar for 5 minutes to 24 hours, preferably about 6 hours, at a temperature of 30 to 80° C., preferably about 50° C. Also, a flow rate of carbon dioxide may be maintained at 10 to 50 g/min, for example, about 30 g/min, but is not particularly limited thereto. The supercritical extraction may be performed once or multiple times (for example, 2 to 4 times). Carbon dioxide containing a ginger extract may be introduced to a middle portion of a separator and a pressure is decreased to about 50 to 60 bar, and thus, the solubility of carbon dioxide is rapidly decreased. The separator has a top end surrounded by a heating jacket having a temperature of about 40° C. and a bottom end surrounded by a cooling jacket having a temperature of about 5° C. or less, and thus, the carbon dioxide containing a ginger extract is divided into an extract and a liquid carbon dioxide at the bottom end and a gaseous carbon dioxide at the top end. The gaseous carbon dioxide at the top end passes through a filter, such as a charcoal filter, is liquefied by a cooler, and is then sent to an extractor by a pump.

According to an embodiment of the present invention, there is provided a pharmaceutical composition including shogaol as an active ingredient. The shogaol is also referred to as 6-shogaol, and a chemical name thereof is (E)-1-(4-hydroxy-3-methoxyphenyl)dec-4-en-3-one. The shogaol is represented by Formula 1 below.

[Formula 1]

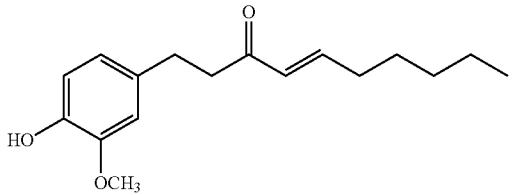

The shogaol may be isolated from ginger, and various synthetic methods are disclosed in, for example, European Patent No. EP1506958.

The pharmaceutical composition according to the present invention includes a pharmaceutically acceptable carrier, and may be formulated into oral dosage form, external dosage form, suppository, and sterile injection solution, such as powders, granules, tablets, capsules, suspensions, emulsions, syrups, or aerosols.

The pharmaceutically acceptable carrier may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil. The pharmaceutical composition may further include a dilluent or an excipient, such as filler, expander, binder, humectant, disintegrant, or surfactant. A solid oral formulation may be a tablet, a pill, a powder, a granule, or a capsule. Such solid formulations may include at least one excipient selected from, for example, starch, calcium carbonate, sucrose, lactose, and gelatin. In addition, such solid formulations may further include a lubricant, such as magnesium stearate or talc. A liquid oral formulation may be a suspension, a solution, an emulsion, or syrup. In addition, the liquid oral formulation may include a dilluent, such as water, liquid paraffine; humectant; sweetening agent; odorant; or preservative. A parenteral formulation may be a sterile aqueous solution, a non-aqueous solution, a suspension, an emulsion, a lyophilized formulation, or a suppository. Non-aqueous solvents or suspending agents may be propylene glycol, polyethylene glycol, natural oil, such as olive oil, or injectable esters, such as ethylolate. Vehicles for suppository can be witepsol, macrogol, Tween 61, cacao butter, Laurin, or glycerogelatine.

In the pharmaceutical composition according to the present invention, a dose of the ginger extract or shogaol may vary depending on patient's state or body weight, seriousness of disease, dosage forms, administration routes, and the period of administration, and can be appropriately determined by a person having ordinary skill in the art. For example, the shogaol may be administered in an amount of 0.01 to 500 mg/kg, preferably 10 to 200 mg/kg, per day. The administration can be completed once or through several times per day. And also, the ginger extract may be administered in an amount of 0.01 to 500 mg/kg, preferably 10 to 200 mg/kg, per day. The administration can be completed once or through several times per day. In the pharmaceutical composition according to the present invention, the amount of the ginger extract or shogaol may be in the range of 0.001 to 50% by weight based on 100% by weight of the pharmaceutical composition.

The present invention includes, within its scope, a food composition for improving learning disorders or memory disorders or alleviating symptoms of learning disorder or memory disorders, which comprises a ginger extract or shogaol as an active ingredient. In addition, the present invention includes, within its scope, a food composition for improving learning or memory, which comprises a ginger extract or shogaol as an active ingredient.

The food composition according to the present invention can be used as a health functional food. According to Article 6727 of Korean Health Functional Food law, the "health functional food" refers to a food which is produced and processed using a source or component that carries out good functions on the human body. The "function" refers to an intake purporting to attain good health effects, that is, a nutrient control with respect to the structure and function of the human body or a physiological operation.

The food composition according to the present invention can include a conventional food additive. The conformity of the "food additive" is determined, as long as there are no other regulations, in consideration with the standard and criteria of the corresponding item according to the general rule of the food additives codex and general tests approved by Korea Food & Drug Administration.

The items listed on the "food additives codex" include a chemically synthesized substance, such as ketone, glycine, potassium citrate, nicotinic acid, or cinnamic acid; natural additives, such as persimmon color, an extract of licorice, crystalline cellulose, caoliang color, or guar gum; or mixed formulation, such as L-sodium glutamate formulation, alkali additives for noodles, preservatives, or tar color formulation.

The food composition according to the present invention may include the ginger extract or shogaol in an amount of 0.01 to 95% by weight, preferably 1 to 80% by weight, based on 100% by weight of the food composition, in order to improve learning disorders or memory disorders or alleviate symptoms of learning disorder or memory disorders; or in order to improve learning or memory. In addition, the food composition may be produced and processed into tablets, capsules, powder, granule, liquid phase, or pills.

For example, in order to produce a health functional food in a tablet form, a mixture of the ginger extract or shogaol, an excipient, a binder, a disintegrant, and other additives can be granulated using a conventional method, and then compression molding process is preformed with a lubricant. Alternatively, the mixture can be directly subjected to the compression molding process. In addition, when needed, the health formulated food in a tablet form may include sweetening agents, and when needed, the health formulated food in a tablet form can be coated with coating materials.

Among health functional foods in a capsule form, a hard capsule formulation can be produced by filling a conventional hard capsule with a mixture of the ginger extract or shogaol and an additive, such as an excipient, or granules of the mixture, or coated granules of the mixture; and a soft capsule formulation can be produced by filling a capsule support of gelatin with a mixture of the ginger extract or shogaol and an additive, such as an excipient. When needed, the soft capsule formulation can include plasticizer, such as glycerin or sorbitol, a coloring agent, and a preservative.

A health functional food in a pill form can be produced by molding a mixture of the ginger extract or shogaol, an excipient, a binder, and a disintegrant using a suitable method. When needed, the health functional food in a pill form can be coated with white sugar or other coating materials, or can be covered with starch, talc, or other materials.

A health functional food in a granule form can be produced by granulating a mixture of the ginger extract or shogaol, an excipient, a binder, and a disintegrant using a suitable method. When needed, the health functional food in a granule form can include a flavoring agent and a sweetening agent.

The excipient, the binder, the disintegrant, the lubricant, the sweetening agent, and the flavoring agent used in the present invention can be defined as corresponding materials having the same or similar functions disclosed in references known in the art (The Korean pharmacopoeia review, Moonsungsa Publication Co., Korea Pharmaceutical University Association, Fifth edition, p33-48, 1989).

The present invention will be described in further detail with reference to the following examples and experimental examples. These examples are for illustrative purposes only and are not intended to limit the scope of the present invention.

EXAMPLE 1

Preparation of Ginger Extract 1 kg of ginger was ground and 5 liters of ethanol was added thereto, ultrasonic extraction was performed thereon for 1 hour, and the resultant solution was filtered to obtain a filtrate. A solid product obtained through the filtering was added to ethanol, ultrasonic extraction was performed thereon for 1 hour, and the resultant solution was filtered to obtain a filtrate. This process was repeatedly performed twice. All of the filtrates were collected and concentrated under reduced pressure, and completely dried by lyophilizing, thereby producing 200 g of ginger extract.

200 g of the obtained ethanol-extract was uniformly suspended by adding 1000 ml of distilled water thereto, and then, 1000 ml of n-hexane was added thereto and the resultant solution was subjected to a fraction process and an n-hexane layer was isolated. The obtained n-hexane layer was concentrated under reduced pressure to remove hexane and dried by lyophilizing. This process was repeatedly performed three times to produce 60 g of a hexane fraction. In addition, 1000 ml of ethyl acetate was added to a residual water layer, and an ethyl acetate layer was isolated. The obtained ethyl acetate layer was concentrated under reduced pressure to remove a solvent and completely dried by lyophilizing. This process was repeatedly performed three times to produce 50 g of an ethyl acetate fraction. Also, 1000 ml of n-butanol was added to a residual water layer, and an n-butanol layer was isolated. The obtained n-butanol layer was concentrated under reduced pressure to remove a solvent and completely dried by lyophilizing. This process was repeatedly performed three times to produce 18 g of an n-butanol fraction. Also, a residual water layer was concentrated under reduced pressure and then lyophilized to produce 43 g of water fraction.

EXAMPLE 2

Preparation of Ginger Extract

A ginger extract was prepared by supercritical extraction. A supercritical extractor was filled with 200 g of a ginger sample that was prepared by grinding and drying ginger, and extraction was performed thereon twice at a pressure of 300 bar and at a temperature of 50□ for 6 hours. In this regard, a flow rate of carbon dioxide was maintained at 30 g/min, and a pressure of an middle portion of a separator was set to 50 to 60 bar, and a temperature of a heating jacket at a top end of the separator was set to 40□ and a temperature of a cooling jacket at a bottom end of the separator was set to 5□ or less. A gaseous carbon dioxide at the top end of the separator passed through a charcoal filter, was liquefied by a cooler, and sent back to the extractor by a pump. As a result, 4.32 g of a ginger extract was obtained.

EXPERIMENTAL EXAMPLE 1

This test was performed using a glioma C6 cell line of a mouse which is known as a cell line that secretes a nerve growth factor (NGF), and a pheochromocytoma PC12 cell line of a mouse which is known as a cell line that grows neurite with respect to an NGF in a similar way as a neuron. C6 cells and PC12 cells were obtained from Korean Cell Line Bank (KCLB Nos. 10107 and 21721, respectively). C6 cells were cultured using DMEM media (Gibco BRL, USA) supplemented with 3.4 g/L of sodium bicarbonate ($NaHCO_3$), 10% fetal bovine serum, and 1% penicillin-streptomycin antibiotics (10000 U/ml), and PC12 cells were cultured using RPMI1640 medium (Gibco BRL, USA) supplemented with 2.0 g/L of sodium bicarbonate, 10% horse serum, 5% fetal bovine serum, and 1% penicillin-streptomycin antibiotics (10000 U/ml). The fetal bovine serum and the horse serum were inactivated at a temperature of 55□ for 30 minutes before use, and all of the cells were cultured in a cell culture vessel with a humidity of 70% at a temperature of 37□ to which 5% carbon dioxide was supplied. Regarding the PC12 cells, the cells were cultured in a culture vessel that was surface-coated with poly-D-lysine (Sigma) diluted with 50 µg/ml of a PBS buffer solution (pH 7.2) for 1 hour and then washed three times with a PBS buffer solution. Shogaol used was obtained from WAKO Company (Japan).

(1) Effect of Ginger Extract on Nerve Growth Factor Secretion Induction in C6 Cells C6 cells attached to a 100 mm culture vessel were separated from the culture vessel by using 0.25% Trypsin-EDTA (Gibco BRL, USA), and then 10 ml of fresh medium was added to the cells to prepare a cell suspension. Then, the number of viable cells was counted and calculated by using a cell number counter. The cells were divided based on the counted cell number such that $2 \times 10^6$ cells were contained in a 100 mm culture dish. After 24 hours of cultivation, the used media was removed and replaced with 10 ml of a DMEM medium containing 2% fetal bovine serum, to which 100 ug/ml of each of the ethanol extract, the n-hexane fraction, the ethyl acetate fraction, the n-butanol fraction, and the water fraction prepared according to Example 1 was added. After 24 hours of cultivation, the respective media were obtained. The obtained media were centrifuged at a rate of 1500 rpm for 10 minutes and then a supernatant was collected, and these media (conditioned media) were used to treat PC12 cells.

The PC12 cells were divided such that $10^5$ cells were contained in each well in a 6-well culture dish. After 24 hours of cultivation, the cells were treated with 2 ng/ml of nerve growth factor diluted with a PBS buffer solution and the conditioned media obtained using C6 cells, the used nerve growth factor and conditioned media were replaced with a fresh nerve growth factor and conditioned media every the other day, and the cells were cultured for 6 days and observed through a microscope. The cells were treated with the conditioned media for 4 days, and 10 cells were randomly selected per well and microscopic images thereof were obtained. The length of neurite was quantified with respect to a diameter of a cell body as follows: if a cell does not have neurite, the length of neurite was set to 0; if the length of neurite is identical to a diameter of a cell body, the length of neurite was set to 1; and if a diameter of a cell body is two times greater than the length of neurite, the length of neurite was set to 2. The test was repeatedly performed three times, and the results are represented as mean±standard deviation in FIG. 1.

Referring to FIG. 1, when the ethanol extract was used, the length of neurite was 2.21±0.13 times greater than the diameter of a cell body; when the n-hexane fraction was used, the length of neurite was 2.35±0.38 times greater than the diameter of a cell body; when the ethyl acetate fraction was used, the length of neurite was 3.24±0.34 times greater than the diameter of a cell body; when the n-butanol fraction was used, the length of neurite was 0.93±0.17 times greater than the diameter of a cell body; and when the water fraction was used, the length of neurite was 0.81±0.19 times greater than the diameter of a cell body. From the results, it was confirmed that the ginger extract has a growth factor secretion activity, and in particular, the ethyl acetate fraction has the largest effects among them.

(2) Effect of Shogaol on Nerve Growth Factor Secretion Induction in C6 cells

The C6 cells were divided and treated with 0.1, 1, 5, 10, and 20 µM of shogaol in the same manner as in Experimental Example 1-1 to prepare conditioned media.

A nerve growth factor secreted from C6 cells by shogaol was quantified by treating a nerve growth factor measurement kit (DY556, R&D system, USA) with the conditioned media. In order to identify an effect of shogaol on nerve growth factor secretion induction, a nerve growth factor in the conditioned media prepared by culturing C6 cells after the cells were treated with shogaol was quantified and the results are shown in FIG. 2.

Figure 2:
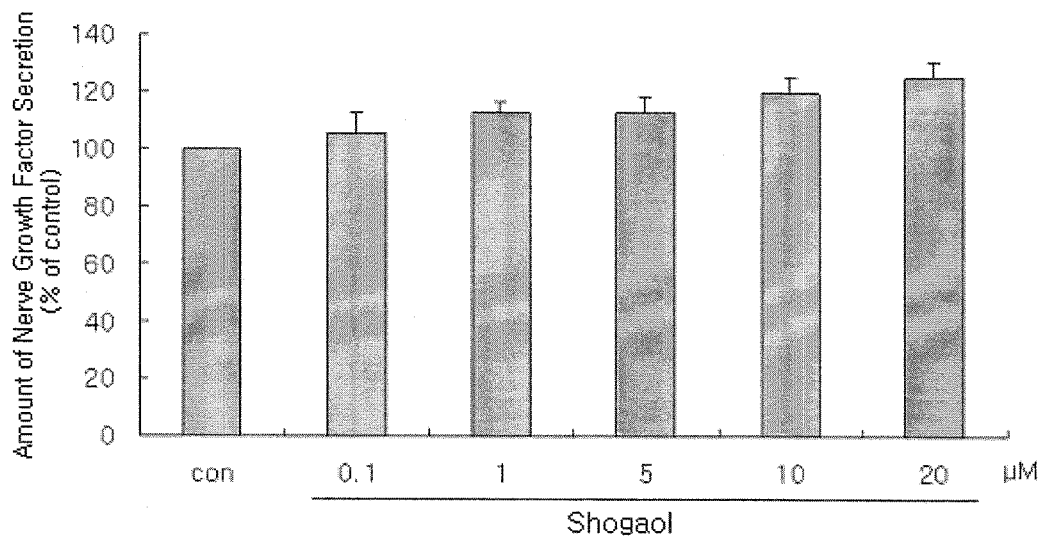
FIG. 2 shows induction of nerve growth factor of shogaol, which were obtained by quantifying a nerve growth factor by using conditioned media obtained by treating 0.1, 1, 5, 10, and 20 µM of shogaol in C6 cells.

Referring to FIG. 2, when 0.1 µM of shogaol was used, a secretion amount of a nerve growth factor was 105.46±7.27% of a control; when 1 µM of shogaol was used, a secretion amount of a nerve growth factor was 112.72±3.67% of a control; when 5 µM of shogaol was used, a secretion amount of a nerve growth factor was 112.97±4.97% of a control; when 10 µM of shogaol was used, a secretion amount of a nerve growth factor was 119.44±5.18% of a control; and when 20 µM of shogaol was used, a secretion amount of a nerve growth factor was 124.81±5.61% of a control. The higher concentration the shogaol had, the secretion amount of a nerve growth factor was concentration-dependently increased and the secretion amount of a nerve growth factor was highest at 20 µM of shogaol. The results above were obtained by repeatedly performing the same experiment three times and were represented as mean±standard deviation.

(3) Effect of Shogaol on Neurite Growth in PC12 Cells

Figure 3:
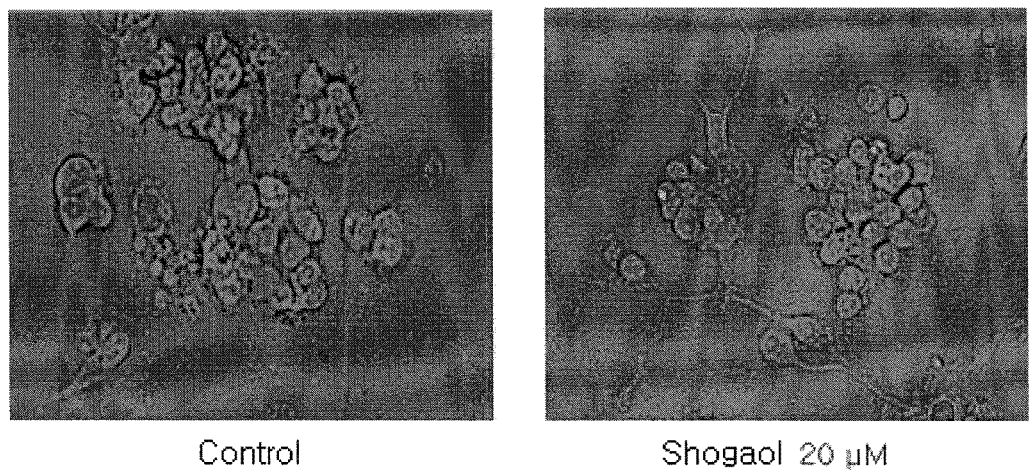
FIG. 3 shows induction of nerve growth factor of shogaol, which were obtained by identifying neurite growth after the conditioned media obtained by treating shogaol in C6 cells were treated in PC12 cells.

PC12 cells were divided and treated in the same manner as in Experimental Example 1-1, and after 24 hours of cultivation, the PC12 cells were treated with a nerve growth factor and conditioned media in the same manner as described above. On the fourth day after the treatment, the PC12 cells were observed using a microscope and the results are shown in FIG. 3. Referring to FIG. 3, when 20 µM of shogaol was used, the growth of neurite of the PC12 cells was increased. This result shows that shogaol has an excellent nerve growth factor secretion activity.

EXPERIMENTAL EXAMPLE 2

Male ICR mice having a weight of 25-28 g were obtained and nurtured in an animal laboratory at Kyunghee University Graduate School of East-West Medicine Science for 7 days for adaptation. Water and feed were freely supplied, and the temperature (22±2□), humidity (53±3%), and a cycle of brightness and darkness (12 hours) were automatically controlled. Shogaol used was obtained from WAKO Company (Japan).

(1) Cognitive Ability Enhancement Effect of Shogaol

Mice were divided into two groups, each of which consisted of 10 mice. A first group (control) was orally administered with 10% dimethyl sulfoxide in an amount of 5 ml per mouse weight kg for 3 days, and a second group was orally administered with 5 mg/kg of shogaol dissolved in 10% dimethyl sulfoxide for 3 days. The oral administration was performed once per day for 3 days, and 1 hour after the last oral administration, a passive avoidance task was performed as follows.

Figure 4:
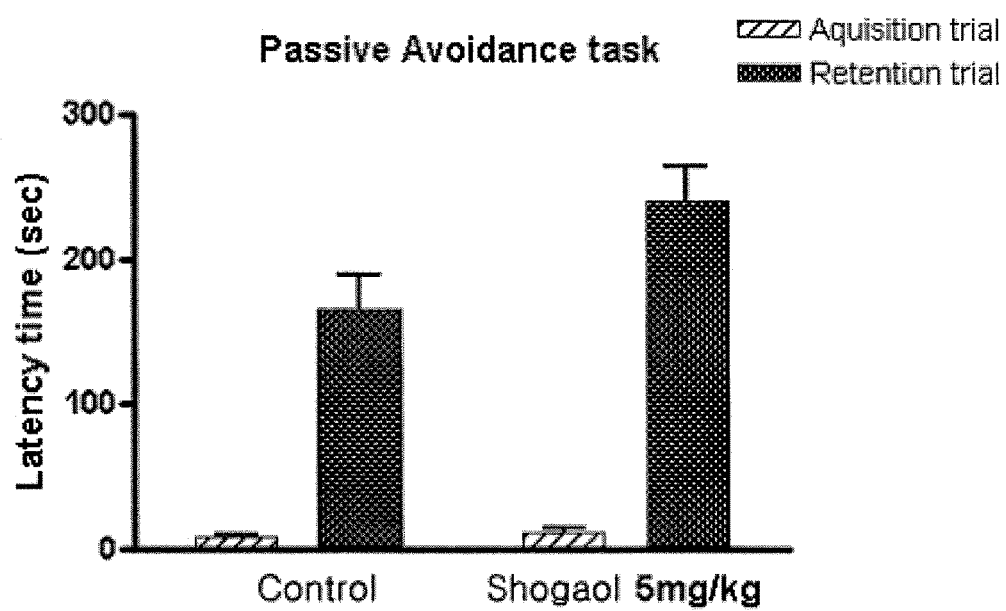
FIG. 4 shows enhancement of cognitive ability of shogaol, which were obtained by performing a passive avoidance task for evaluating cognitive ability increase after 5 mg/kg of shogaol was administered to ICR mice.

In a test device having an inner structure divided into two identical spaces with a door therebetween, on a first day, one space was bright and the other space was dark, and a test animal was allowed to stay in the bright space for 10 seconds and then the door was opened, and when the test animal moved toward the dark space, 0.25 mA of an electrical stimulation was applied to the feet of the test animal. After 24 hours, the same passive avoidance task was performed and a time during which the test animal stayed in the light space was measured. The results are shown in FIG. 4.

The latency time of the control was 165.50±23.39 seconds, which indicates that a memory generated by electrical stimulation was maintained, and the latency time of the group to which 5 mg/kg of shogaol was administered was 240.63±24.14 seconds. That is, the administration of shogaol significantly increased the latency time (p<0.05).

(2) Cognitive Ability Enhancement Effect of Ginger Extract

Figure 5:
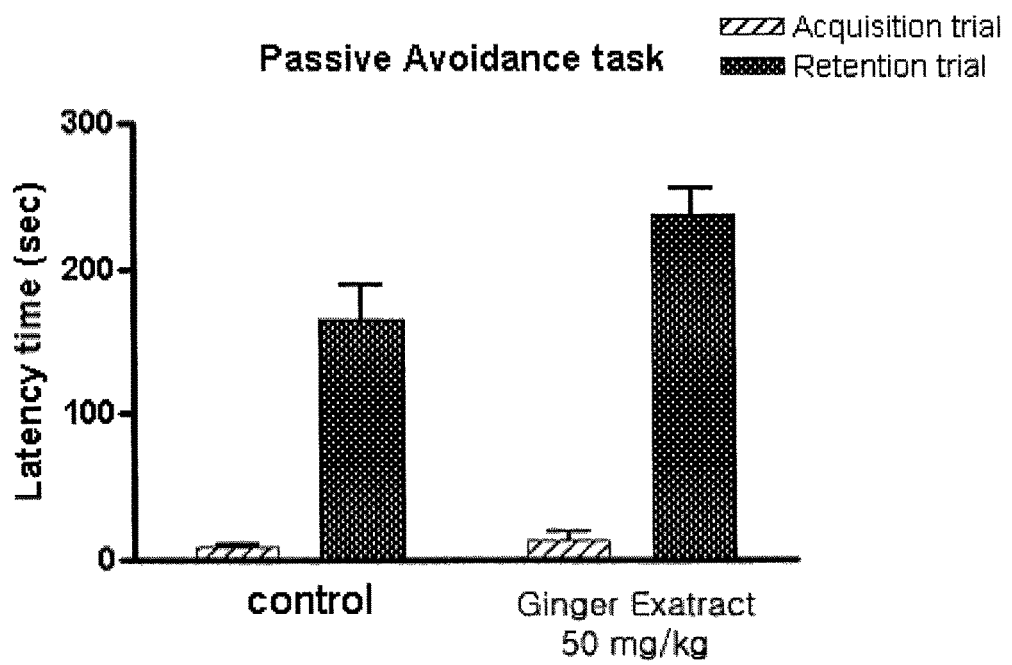
FIG. 5 shows enhancement of cognitive ability of a ginger extract, which were obtained by performing a passive avoidance task for evaluating cognitive ability increase after 5 mg/kg of a ginger extract was administered to ICR mice.

Mice were divided into two groups, each of which consisted of 10 mice. A first group (control) was orally administered with 10% dimethyl sulfoxide in an amount of 5 ml per mouse weight kg for 3 days, and a second group was orally administered with 50 mg/kg of the ginger extract (the ginger extract prepared according to Example 2) dissolved in 10% dimethyl sulfoxide for 3 days. The oral administration was performed once per day for 3 days, and 1 hour after the last oral administration, a passive avoidance task was performed in the same manner as in Experimental Example 2-1. The results are shown in FIG. 5.

The latency time of the control was 165.50±23.39 seconds, which indicates that a memory generated by electrical stimulation was maintained, and the latency time of the group to which 50 mg/kg of the ginger extract was administered was 237.43±17.35 seconds. That is, the administration of the ginger extract significantly increased the latency time (p<0.05).

EXPERIMENTAL EXAMPLE 3

Protective Effect of Shogaol and Ginger Extract in Rat Fetal Mesencephalon Cells with respect to Neurotoxicity of MPP+ (1-methyl-4-phenylpyridinium) and 6-OHDA (6-hydroxy-dopamine)

Female Sprague-Dawley rats (2-week old) were used, and shogaol was obtained from WAKO Company (Japan).

Fetal mesencephalon tissues of Sprague-Dawley rats (2-week old) were desquamated, and mechanically dissociated by using a forcept. The tissues were treated with trypsin and the number of cells was counted, and the cells were seeded on a cover slip coated with poly-L-lysine (PLL), and then proliferated in an incubator including 5% $CO_2$ and 95% air at a temperature of 37□ for 5 days. A fetal bovine serum (FBS)-free media was treated with 0.01 μM or 0.1 μM of shogaol after the shogaol was diluted, or the ginger extract (the ethanol extract, the hexane fraction, the ethyl acetate fraction, the butanol fraction, and the water fraction prepared according to Example 1) after the ginger extract was diluted. 10 μM of MPP+ was used for 23 hours, one hour after the treatment with shogaol; and 10 μM of 6-OHDA was used for 18 hours, 6 hours after the treatment with shogaol. The cells were immobilized using 4% paraformaldehyde (PFA) and washed with phosphate buffer saline (PBS).

(1) Evaluation of Protective Activity of Shogaol—Immunohistochemistry

Cells immobilized by using 4% PFA were washed with PBS and then, dehydrated with 1% hydrogen peroxide for 15 minutes. Then, PBS, 3% triton X-100, and normal goat serum-containing tyrosine hydroxylase (TH, millipore, rabbit origin 1:2000) were reacted with the cells overnight. After a predetermined period of time, the cells were reacted with biotinylated anti-rabbit (vector, goat origin) as a secondary antibody, underwent an ABC reaction (ABC kit, vector), and were color-produced by using diaminobenzidine (DAB). After the color-producing using DAB, a cover slip was separated and then mounted on a slide by using a gel mount and the number of cells was counted. The results are shown in FIGS. 6 and 7.

Figure 6:
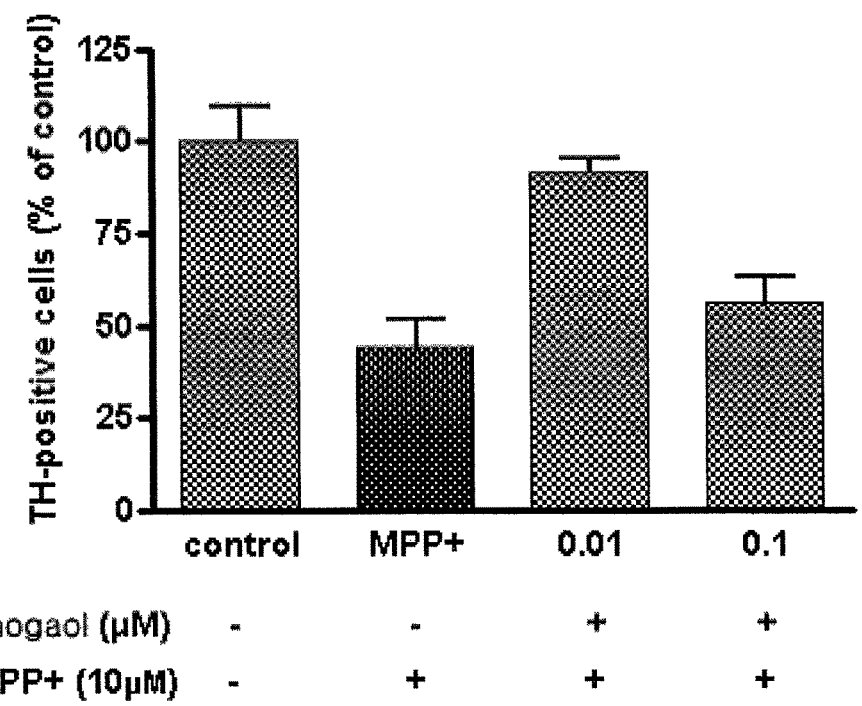
FIG. 6 shows protective effects of shogaol on MPP+ induced neuronal damage in rat primary mesencephalic dopaminergic cells.

FIG. 6 shows dopamine cells protective effects of shogaol with respect to neurotoxicity of MPP+. In the case of a MPP+ group, the number of dopamine positive cells was 44.25±7.61% of a control. That is, the number of dopamine cells was significantly reduced (p<0.01). However, when the cells were treated with shogaol, at a concentration of 0.01 μM, the number of dopamine positive cells was 91.50±3.38%. That is, shogaol showed significant dopamine cells protective effects (p<0.05).

Figure 7:
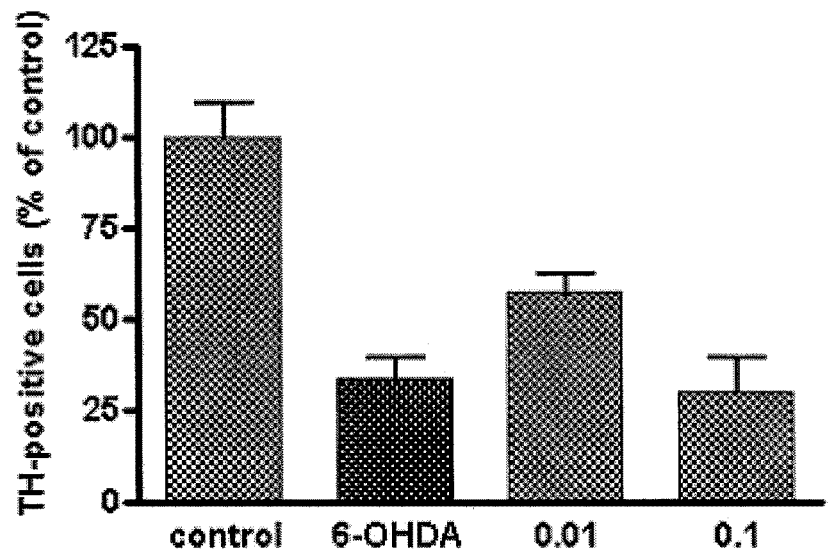
FIG. 7 shows protective effects of shogaol on neurotoxicity of 6-OHDA in rat primary mesencephalic dopaminergic cells.

FIG. 7 shows dopamine cells protective effects of shogaol with respect to neurotoxicity of 6-OHDA. In the case of a 6-OHDA group, the number of dopamine positive cells was 34.00±5.77% of the control. That is, the number of dopamine cells was significantly reduced (p<0.001). However, when the cells were treated with shogaol at a concentration of 0.01 μM, the number of dopamine positive cells was 57.25±5.65%. That is, the number of dopamine positive cells was increased compared to the 6-OHDA group.

(2) Evaluation of Protective Activity of Ginger Extract—Immunohistochemistry

Figure 8:
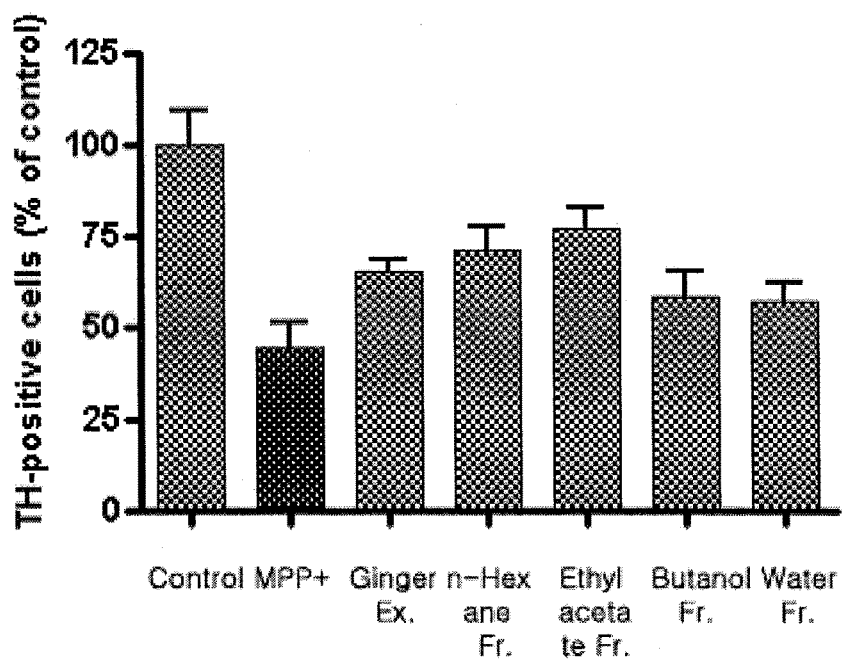
FIG. 8 shows protective effects of a ginger extract on neurotoxicity of MPP+. in rat primary mesencephalic dopaminergic cells.
Figure 9:
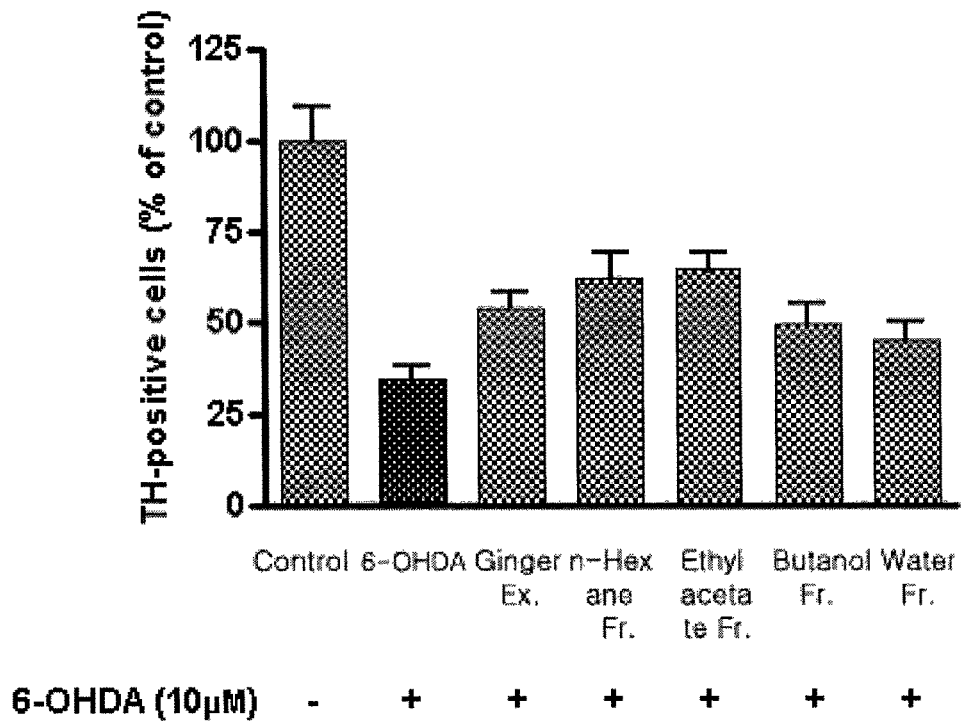
FIG. 9 shows protective effects of a ginger extract on neurotoxicity of 6-OHDA.in rat primary mesencephalic dopaminergic cells.

Cells were color-produced by immunohistochemistry in the same manner as Experimental Example 3-1, and the number of cells was counted and the results are shown in FIGS. 8 and 9.

FIG. 8 shows dopamine cells protective effects of a ginger extract with respect to neurotoxicity of MPP+. In the case of a MPP+ group, the number of dopamine positive cells was 44.25±7.61% of a control. That is, the number of dopamine cells was significantly decreased (p<0.01), and when 100 ug/ml of each of a ginger extract (ethanol extract), a hexane fraction, an ethyl acetate fraction, a butanol fraction, and a water fraction was used, the numbers of dopamine positive cells were 65.20±3.45%, 71.41±6.32%, 76.60±6.15%, 58.32±7.22%, and 57.17±5.33%, respectively. That is, when a ginger extract was used, the number of dopamine positive cells was increased compared to the MPP+ group.

FIG. 9 shows dopamine cells protective effects of a ginger fraction with respect to neurotoxicity of 6-OHDA. In the case of a 6-OHDA group, the number of dopamine positive cells was 34.00±5.77% of a control. That is, the number of dopamine cells was significantly decreased (p<0.001). When 100 ug/ml of each of a ginger extract (ethanol extract), a hexane fraction, an ethyl acetate fraction, a butanol fraction, and a water fraction, the numbers of dopamine positive cells were 54.20±4.31%, 62.50±6.94%, 64.54±4.67%, 49.61±5.64%, and 45.11±5.21%, respectively. That is, when a ginger extract was used, the number of dopamine positive cells was increased compared to the 6-OHDA group.

EXPERIMENTAL EXAMPLE 4

Protective Effect Evaluation of Ginger Extract and Shogaol on C57BL/6 Mouse having Parkinson's disease Induced by MPTP (N-methyl-4-phenyl-1,2,3,6-tetrahydropyridine) Administration 7-week old C57BL/6 based male mice (19-22 g) were obtained and nurtured in an animal laboratory at Kyunghee University Graduate School of East-West Medicine Science for one week or more for adaptation. Water and feed were freely supplied, and the temperature (22±2□), humidity (53±3%), and a cycle of brightness and darkness (12 hours) were automatically controlled. Shogaol used was obtained from WAKO Company (Japan).

(1) Protective Effects of Shogaol on MPTP Administration-induced Parkinson's disease Model Mice were divided into three groups, each of which consisted of 6 mice. A first group (control) and a second group (MPTP group) were orally administered once per day with 10% dimethyl sulfoxide in an amount of 5 ml per mouse weight kg for 5 days, and a third group (shogaol-administered group) was orally administered once per day with 10 mg/kg of shogaol dissolved in 10% dimethyl sulfoxide for 5 days. 2 hours after the oral administration, the first group (control) was intraperitoneally administered with saline in an amount of 5 ml per mouse weight kg for 5 days, and the second and third groups were intraperitoneally administered with 30 mg/kg of MPTP dissolved in saline for 5 days.

(1-1) Pole Test

On a day after the last day of the 5-day administration period, a pole test was performed using a pole having a height of 50 cm and a diameter of 1 cm. A C57bl/6 mouse was placed on the pole with its head upward, and a time during which the mouse turns a summit of the pole at an angle of 180° and moves downward until its four feet touch the ground was measured. Each mouse practiced three times and then, the pole test was performed 5 times, and the results are shown in FIG. 10.

Figure 10:
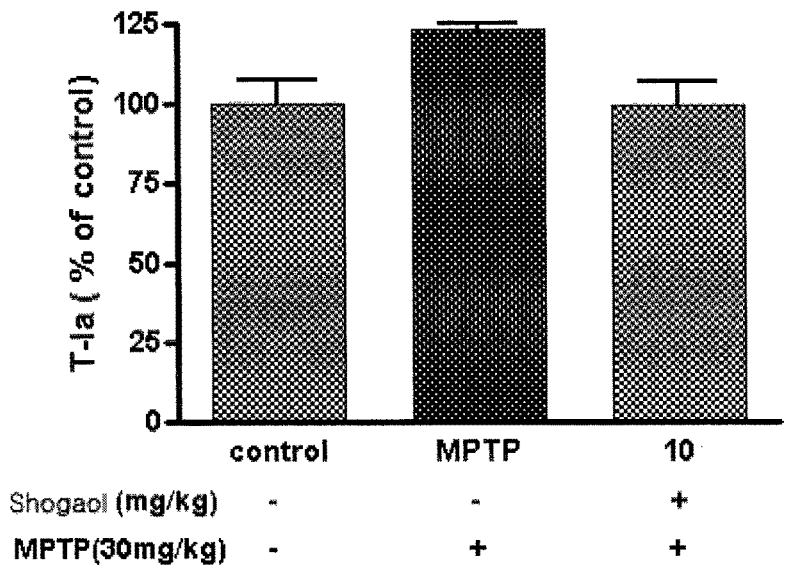
FIG. 10 shows pole test results of shogaol with respect to a C57BL/6 mouse having MPTP-induced Parkinson's disease.

Referring to FIG. 10, when shogaol was used, T-la (% of control) was 99.10±8.11 seconds, which is a level similar to a control to which MPTP was not administered. Accordingly, it was confirmed that shogaol recovered MPTP-induced bradykinesia to an almost normal level (p<0.05).

(1-2) Dopamine Cell Protective Activity Evaluation

The mice of the respective groups were sacrificed after the pole test was completely performed, and brain tissues (striatum and substantia nigra) were isolated. The isolated brain tissues were dehydrated with hydrogen peroxide and reacted with tyrosine hydroxylase (TH, millipore, rabbit origin 1:2000) as a primary antibody overnight, and then a biotinylated anti-rabbit (vector, goat origin) was used as a secondary antibody, and the tissues underwent an ABC reaction (ABC kit, vector), and were color-produced by using diaminobenzidine. Dopamine cells protective effects were confirmed by measuring an optical density of striatum and counting the number of TH positive cells in substantia nigra. The results are shown in FIGS. 11 and 12.

Figure 11:
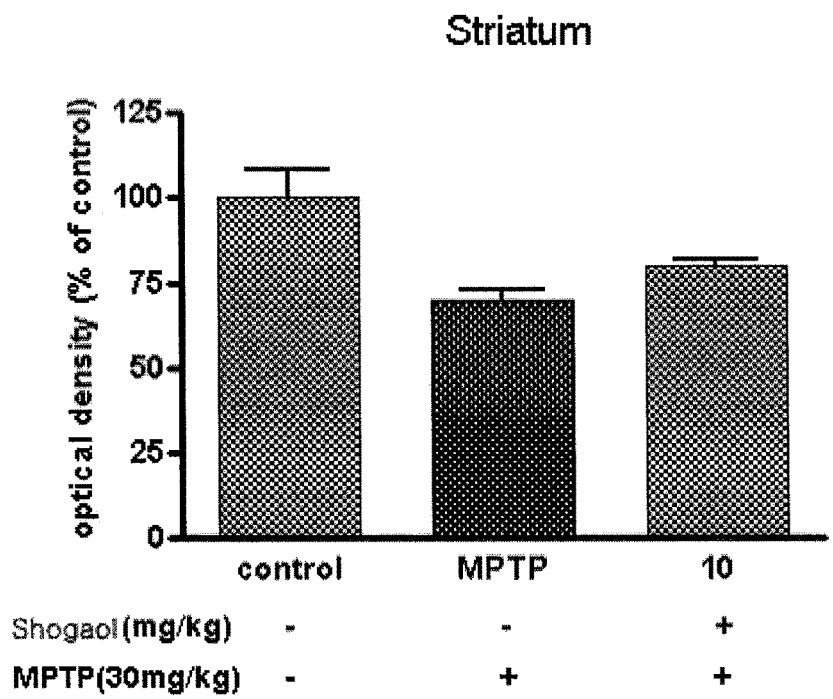
FIG. 11 shows the suppressive activity of shogaol with respect to an optical density decrease of immuoreactivity of tyrosine hydroxylase in striatum of a C57BL/6 mouse having MPTP-induced Parkinson's disease.
Figure 12:
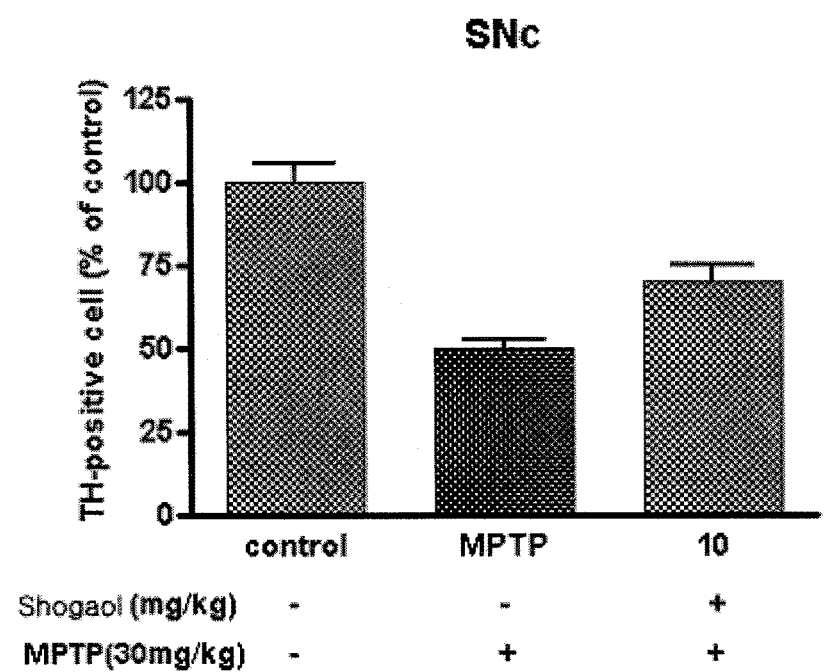
FIG. 12 shows the suppressive activity of shogaol with respect to a decrease of dopaminergic cells (tyrosine hydroxylase immuoreactive cells) in substantia nigra of a C57BL/6 mouse having MPTP-induced Parkinson's disease.

Referring to FIGS. 11 and 12, when shogaol was used, an optical density of striatum was 80.11±1.97% of a control. That is, the dopamine cell protection activity was significant compared to a MPTP-administered group (p<0.05). When shogaol was used, the number of TH positive cells in substantia nigra was 70.30±4.86 of a control. That is, the number of TH positive cells was significantly increased compared to the MPTP-administered group (p<0.05). From the results, it was confirmed that shogaol had excellent dopamine cell protection activities in striatum and substantia nigra.

(2) Protective Effects of Ginger Extract on MPTP Administration-Induced Parkinson's disease Model Mice were divided into three groups, each of which consisted of 10 mice. A first group (control) and a second group (MPTP group) were orally administered once per day with 10% dimethyl sulfoxide in an amount of 5 mL per mouse weight kg for 5 days, and a third group (ginger extract-administered group) was orally administered once per day with 50 mg/kg of a ginger extract (the extract prepared according to Example 2) dissolved in 10% dimethyl sulfoxide for 5 days. 2 hours after the oral administration, the first group (control) was intraperitoneally administered with saline in an amount of 5 ml per mouse weight kg for 5 days, and the second and third groups were intraperitoneally administered with 30 mg/kg of MPTP dissolved in saline for 5 days.

(2-1) Pole Test

Figure 13:
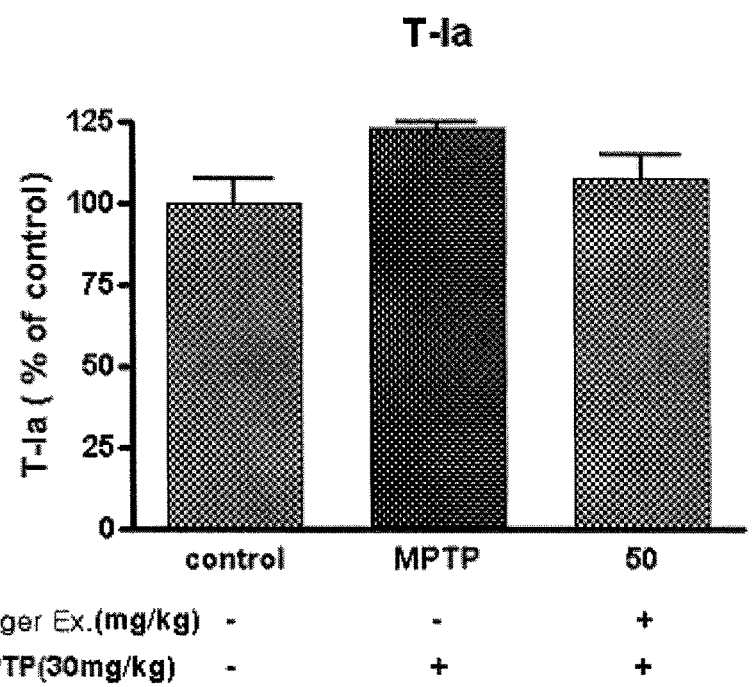
FIG. 13 shows pole test results of a ginger extract with respect to a C57BL/6 mouse having MPTP-induced Parkinson's disease.

On a day after the last day of the 5-day administration period, a pole test was performed in the same manner as in (1-1) above, and the results are shown in FIG. 13. Referring to FIG. 13, when a ginger extract was administered, T-la was 107.48±7.32 seconds, and thus, it was confirmed that the ginger extract recovered MPTP-induced bradykinesia.

(2-2) Dopamine Cell Protection Activity Evaluation

Figure 14:
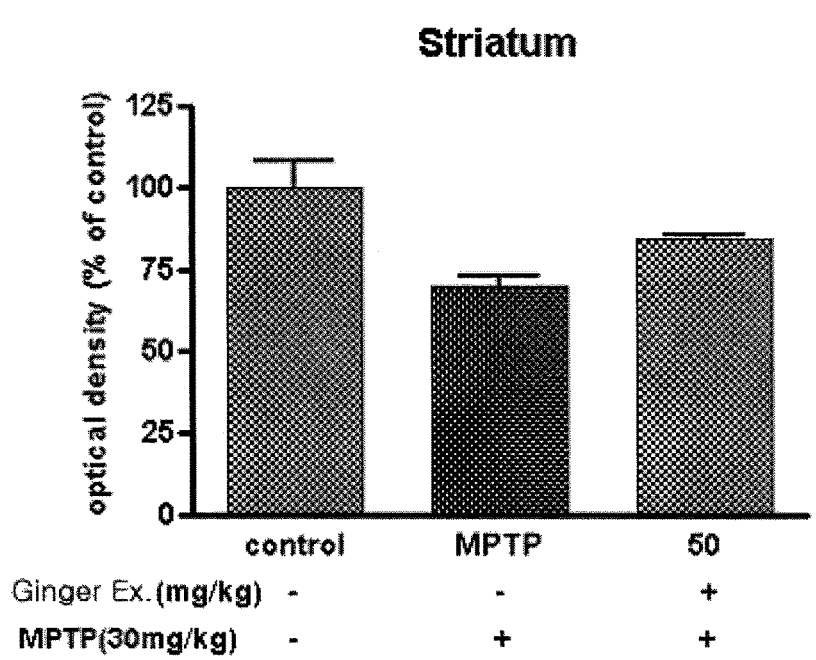
FIG. 14 shows measurement results of a suppressive activity of a ginger extract with respect to an optical density decrease of immuoreactivity of tyrosine hydroxylase in striatum of a C57BL/6 mouse having MPTP-induced Parkinson's disease.
Figure 15:
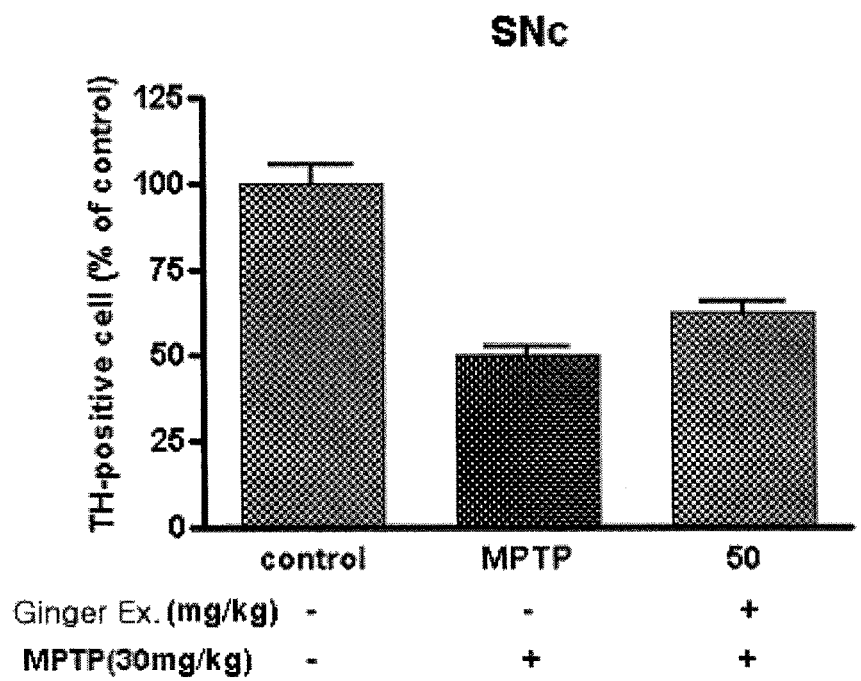
FIG. 15 shows the suppressive activity of a ginger extract with respect to a decrease of dopaminergic cells (tyrosine hydroxylase immuoreactive cells) in substantia nigra of a C57BL/6 mouse having MPTP-induced Parkinson's disease.

The mice of the respective groups were sacrificed after the pole test was completely performed, and brain tissues (striatum and substantia nigra) were isolated. Protection activity was evaluated using the isolated brain tissues in the same manner as in (1-2) above, and the results are shown in FIGS. 14 and 15. Referring to FIGS. 14 and 15, when a ginger extract was administered, an optical density of striatum was 84.21±1.48% of a control. That is, it was confirmed that dopamine cell protection activity was significant compared to a MPTP-administered group (p<0.01). When a ginger extract was administered, the number of TH positive cells in substantia nigra was 62.20±3.67%. That is, the number of TH positive cells was significantly increased compared to the MPTP-administered group (p<0.05). From the results, it was confirmed that the ginger extract had excellent dopamine cell protection activities in striatum and substantia nigra.

EXPERIMENTAL EXAMPLE 5

Ginger Extract Activity Evaluation on 2-Vessel Occlusion Cerebral Ischemia Model 7-week old C57BL/6 based male mice (19-22 g) were obtained and nurtured in an animal laboratory at Kyunghee University Graduate School of East-West Medicine Science for one week or more for adaptation. Water and feed were freely supplied, and the temperature (22±2□), humidity (53±3%), and a cycle of brightness and darkness (12 hours) were automatically controlled.

Mice were divided into three groups, each of which consisted of 10 mice. Anesthesia was induced in an anesthetic gas ($O_2$: 30%, $N_2O$: 70%, and isoflurane: 2.0%) chamber, and mice of the respective groups were located on an operating table with their backs on the operating table. The skin of each mouse was cut upward by about 1.5 cm from a point where the upper limbs and an intermediate line meet, and then, facing common carotid arteries were exposed without damage of tissues. Tissues and nerves attached to the carotid arteries were dissociated and occlusion was performed thereon by using an aneurism clip for 25 minutes. In this regard, the temperature of the mice was measured by using a rectal thermometer and maintained at 37±0.5 □.

A sham control refers to a group obtained as described above except for the occlusion of the common carotid arteries. Medicine administration was performed immediately after a 2VO step, and thereafter, performed once per day for 3 days. The Sham control and a 2VO step group were administered with 10% tween 80, and with 25 mg/kg of a ginger extract and the fractions (prepared in Example 1) dissolved in 10% tween 80. 7 days after the step, the mice were put under anesthesia by using pentobarbital sodium (60 mg/kg, i.p.) and then perfusion was performed thereon using 4% paraformaldehyde. The brain was extracted and then fixed with 4% paraformaldehyde and immersed in a 30% sucrose solution for one day. Then, the brain was frozen and vertically cut to a size of 30 μm. The cut tissue was placed on a gelatin-coated slide and stained with 0.5% cresyl violet. The number of neurons in an intermediate zone of CA1 portion of hippocampus which is very susceptible to delayed neuroblast death was identified. This identification was performed by counting the number of cells stained at a high magnification rate (×400).

Figure 16:
FIG. 16 shows efficacy of a ginger extract with respect to ischemia-induced neuron apoptosis in hippocampus of a 2-vessel occlusion cerebral ischemia model.
Figure 17:
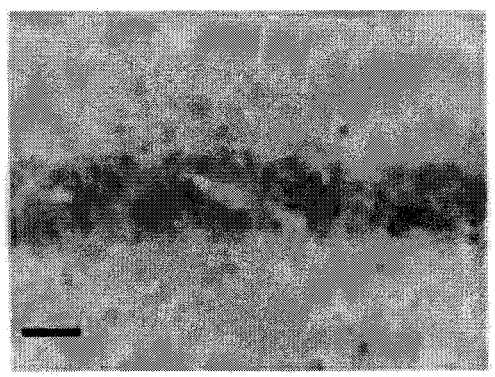
FIG. 17 shows enlarged images of an intermediate zone of CA1 of hippocampus of a 2-vessel occlusion cerebral ischemia model in which neuron apoptosis occurred.
Figure 17:
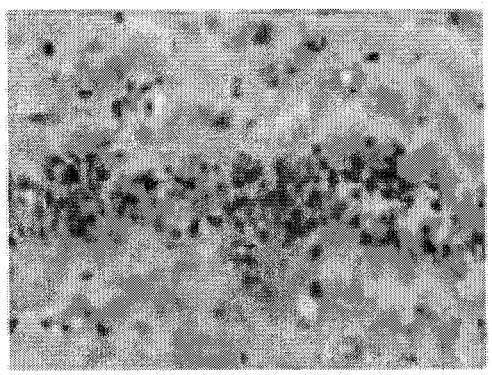
Figure 17:
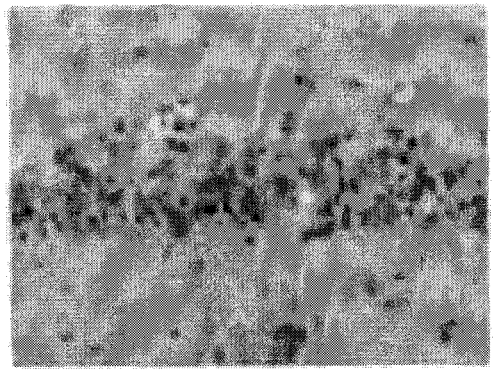
Figure 18:
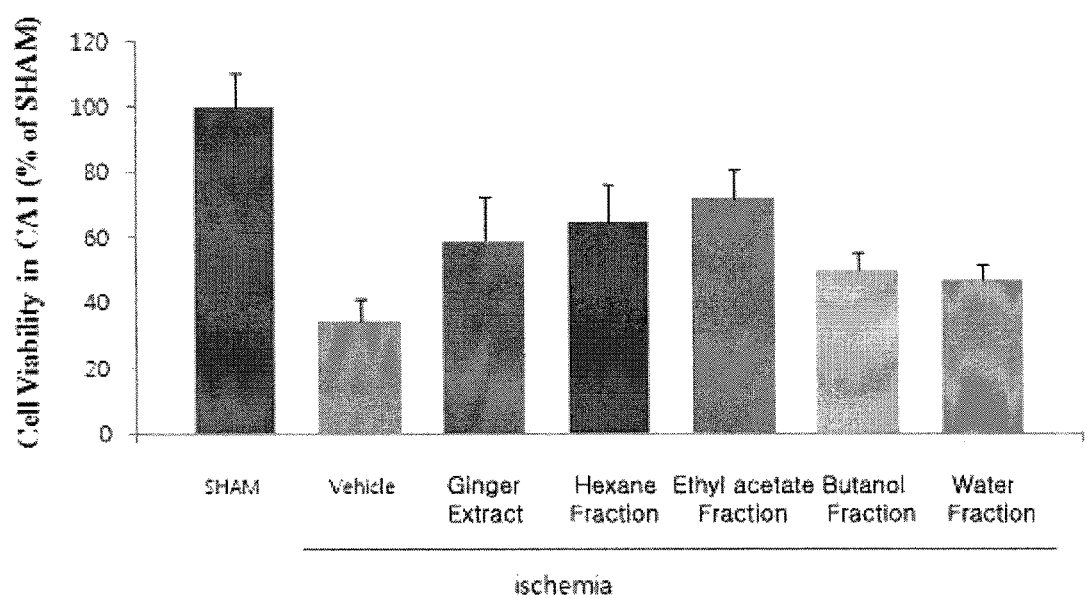
FIG. 18 shows cell viability in CA1 of a ginger extract and fractions.

Hippocampus staining results of the mice of the respective groups are shown in FIG. 16. Referring to FIG. 16, it was confirmed that apoptosis occurred in CA1 of hippocampus on which 2VO step was performed, and apoptosis in CA1 was suppressed by the ginger extract. FIG. 17 shows an enlarged image of an intermediate zone of CA1 of the hippocampus and FIG. 18 shows results of a cell viability rate in CA1. Referring to FIG. 18, it was confirmed that a ginger extract (ethanol extract), an n-hexane fraction, an ethyl acetate fraction, a butanol fraction, and a water fraction-treated groups suppressed neuron apoptosis in CA1. A neuron apoptosis suppression efficacy of the ginger extract, the n-hexane fraction, the ethyl acetate fraction, the butanol fraction, and the water fraction was respectively 24.6±13.1%, 30.2±11.5%, 37.5±8.5%, 15.6±5.3%, and 12.5±4.7% of the 2VO step group.

EXPERIMENTAL EXAMPLE 6

Shogaol Activity Evaluation in 2-vessel Occlusion Cerebral Ischemia Model

Figure 19:
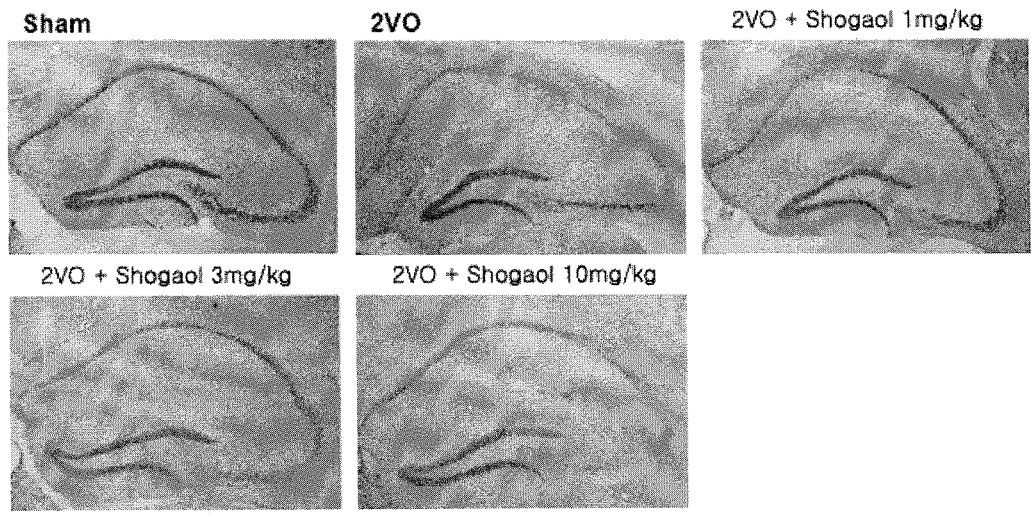
FIG. 19 shows efficacy of shogaol with respect to ischemia-induced neuron apoptosis in hippocampus of a 2-vessel occlusion cerebral ischemia model.
Figure 20:
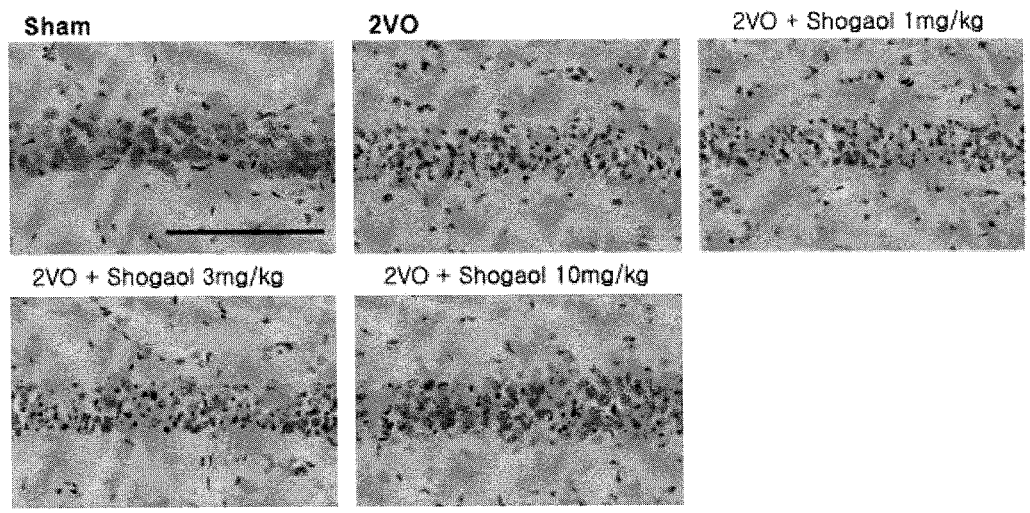
FIG. 20 shows enlarged images of an intermediate zone of CA1 of hippocampus of a 2-vessel occlusion cerebral ischemia model in which neuron apotosis occurred.
Figure 21:
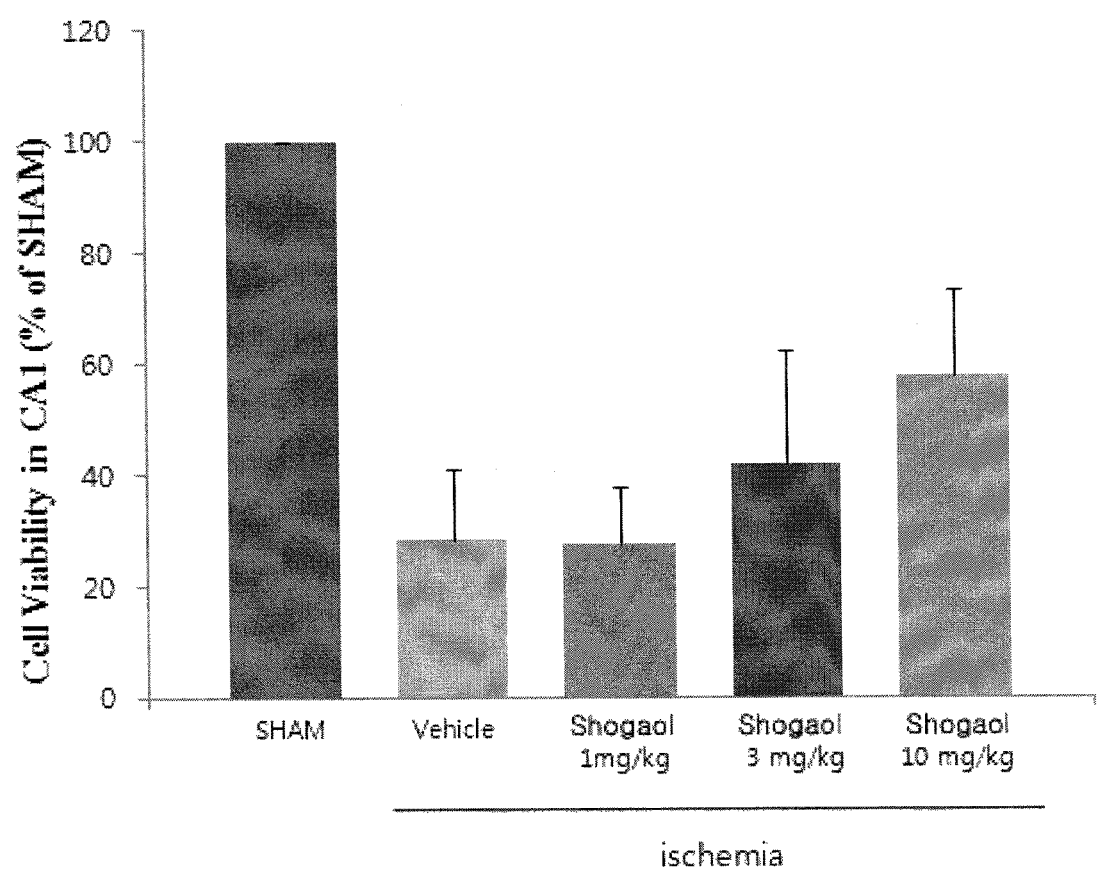
FIG. 21 shows cell viability of shogaol in CA1.

Mice were divided into three groups, each of which consisted of 10 mice. A 2VO step was performed in the same manner as in Experimental Example 1. A sham control was obtained as described above in which common carotid arteries were not occluded. Medicine administration was performed immediately after the 2VO step, and thereafter, performed once per day for 3 days. The Sham control and a 2VO step group were administered with 10% tween 80, and with 1, 3, and 10 mg/kg of shogaol dissolved in 10% tween 80. Shogaol showed neuron apoptosis suppression efficacy of 29.5±15.4% of the 2VO step group at a concentration of 10 mg/kg (see FIGS. 19, 20, and 21).

EXPERIMENTAL EXAMPLE 7

Toxicity Test (1) Acute Toxicity Test

The ginger extract and shogaol prepared according to Examples 1 and 2 were sequentially administered in a dosage of 0.1 mg/10 ml/kg to 5000 mg/10 ml/kg to SD rats (three female rats and three male rats), and a death rate, general symptom, and weight of the rats, and a rat autopsy opinion were evaluated for 2 weeks. As a result, no rats died during the test period. Regarding the general symptom, abnormal symptoms with respect to a test material were not found, and regarding a body weight, weight change with respect to a test material did not occur. Also, regarding macroscopic autopsy opinion, abnormal findings with respect to a test material were not found. Accordingly, it was confirmed that ginger extract and shogaol all had stability at a dosage of at least 5 g/kg.

(2) Back Mutation Test

In order to evaluate genotoxicity in bacteria, a back mutation test was performed using histidine-requiring *salmonella typhimurium* strains (TA 100, TA 1535, TA 98, and TA 1537) and an *E. coli* strain (*E. coli* WP2 uvrA). As a result, a positive control has a substantially greater colony number than a negative control. However, in test material-treated groups of all strains (that is, groups treated with the extract and shogaol prepared according to Examples 1 and 2), the colony number was not increased. Accordingly, it was confirmed that the ginger extract and shogaol all had stability in the genotoxicity test.

The invention claimed is:

1. A method of treating Parkinson's disease in a subject in need thereof, comprising administering to the subject a composition comprising an effective amount of 6-shogaol having the following Formula 1:

[Formula 1]

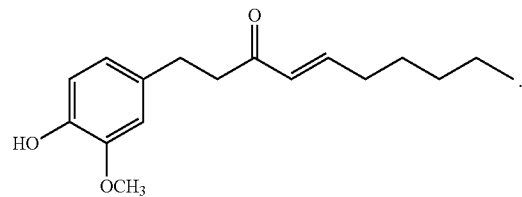

2. The method of claim 1, wherein the composition is administered an oral dosage form selected from the group consisting of powder, granule, tablet, suspension, emulsion, and syrup.

3. The method of claim 1, wherein the composition is a pharmaceutical composition further comprising a pharmaceutically acceptable carrier.

4. The method of claim 1, wherein the composition is a food composition further comprising a food additive.

* * * * *